United States Patent [19]

Matsumoto et al.

[11] Patent Number: 5,322,955
[45] Date of Patent: Jun. 21, 1994

[54] METHOD OF MANUFACTURING 3-DPA-LACTONE

[75] Inventors: Katsuya Matsumoto; Takashi Ebata; Hiroshi Kawakami; Koshi Koseki; Hajime Matsushita, all of Yokohama, Japan

[73] Assignee: Japan Tobacco, Inc., Tokyo, Japan

[21] Appl. No.: 938,238

[22] PCT Filed: Feb. 21, 1992

[86] PCT No.: PCT/JP92/00186

§ 371 Date: Oct. 22, 1992

§ 102(e) Date: Oct. 22, 1992

[87] PCT Pub. No.: WO92/14721

PCT Pub. Date: Sep. 3, 1992

[30] Foreign Application Priority Data

Feb. 22, 1991 [JP] Japan .................................. 3-028882

[51] Int. Cl.$^5$ ............................................. C07D 233/00
[52] U.S. Cl. ....................................................... 549/313
[58] Field of Search ............................................. 549/313

[56] References Cited

U.S. PATENT DOCUMENTS 2,359,096  9/1944  Elderfield ............................ 549/313
2,359,208  9/1944  Elderfield et al. ................... 549/313

OTHER PUBLICATIONS

Sakata, Toshiie et al, Brain Res. Bull., vol. 5 (Suppl. 4) pp. 23-28, 1980.
Shimizu, Nobuaki et al, Am. J. Physiol., 246, pp. 542-550, 1984.
Sakata, Toshiie, Brain Res. Bull., vol. 25, pp. 969-974, 1990.
Matsumoto, Katsuya et al, Heterocycles, vol. 34, No. 2, pp. 363-367, 1992.
Uchikawa, Osamu et al, Bull. Chem. Soc. Jpn., 61, pp. 2025-2029, 1988.
Bock, Klaus et al, Acta Chemica Scandinavica, B 35, pp. 155-162, 1981.

*Primary Examiner*—C. Warren Ivy
*Assistant Examiner*—Raymond Covington
*Attorney, Agent, or Firm*—Birch, Stewart, Kolasch & Birch

[57] ABSTRACT

In the method of the present invention for manufacturing 3-DPA-lactone, a protective group is introduced in the first step into the hydroxyl group at 4-position of γ-ribonolactone by an ordinary method. Then, an acid anhydride or an acid chloride is added in the presence of a tertiary amine compound so as to conduct a β-elimination of the hydroxyl group at the 3-position. As a result, a double bond is formed between the 2- and 3-positions and, at the same time, the hydroxyl group at the 2-position is acylated. The double bond between the 2- and 3-positions is reduced in the next step by means of a catalytic hydrogenation. Finally, the protective group of the hydroxyl group is eliminated by an ordinary method. The particular method permits using readily available raw materials, decreasing the number of manufacturing steps, and easily and selectively synthesizing the desired 3-DPA-lactone, which is hardly obtained from nature in a large amount, in high yield, compared with the conventional method.

14 Claims, No Drawings

METHOD OF MANUFACTURING 3-DPA-LACTONE

TECHNICAL FIELD

The present invention relates to a method of manufacturing 3-DPA-lactone.

BACKGROUND ART

In recent years, saccharide-containing compounds and saccharide-like compound have attracted attention as useful physiologically active substances in the field of fine chemicals such as medicines and agricultural chemicals. As one of such saccharide-like compounds, known is (2S, 4S)-2-hydroxy-4-hydroxymethyl-4-butanolide (3-DPA-lactone) of chemical structure of formula (V) given below:

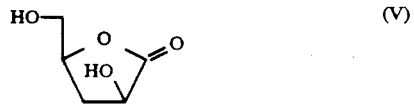
(V)

The compound 3-DPA-lactone is present in the body fluid of an animal. An increase in the concentration of the compound in the blood is observed in a hungry rat. Also, an ingestive action or appetite is induced by the administration of the compound. Such being the situation, 3-DPA-lactone is known as an endogenous appetite-promoting substance, as described in "H. Ohmura, N. Shimizu (Kagaku to Seibutsu), Vol. 22, No. 4, page 228, and its reference article, O. Uchikawa, N. Okukado, T. Sakata, K. Arase, Bull. Chem. Soc. Jpn., 61, 2025 (1988)".

Thus, 3-DPA-lactone is indispensable for the scientific clarification of the ingestive action of animals including human beings. It is possible to widely apply the clarified mechanism for the development of food, medicines and agricultural chemicals. It is also possible to promote the growth of livestock by adding an appetite-promoting substance to the feed for the livestock and using its appetite-promoting effect.

Only traces of 3-DPA-lactone are present in nature, making it difficult to obtain a large amount of the compound by extraction from natural materials. In other words, it is necessary to employ a synthetic technique for obtaining a large amount of 3-DPA-lactone.

Presently, a method of manufacturing 3-DPA-lactone, in which L-malic acid having an optical activity is used as the starting material, is known to the art, as described in "O. Uchikawa, N. Okukado, T. Sakata, K. Arase, K. Terada, Bull. Chem. Soc. Jpn., 61, 2025 (1988)". Also known is a method using γ-ribonolactone as the starting material, as described in "K. Bock, I. Lundt, C. Pedersen, Acta. Chem. Scand., B85, 155 (1981)". In the known method using L-malic acid as the starting material, a vinyl group is introduced by Grignard reaction to the carbonyl group of (S)-3,4-0-isopropylidene-3,4-dihydroxy butanal so as to form a hydroxyl group at the 2-position of 3-DPA-lactone, followed by cleaving the vinyl group in an oxidizing manner by Sharpless method so as to form a carboxyl group and, thus, to form γ-lactone.

However, the Grignard reaction employed in the known method described above is not stereoselective, with the result that two kinds of diastereomers are formed with respect to the hydroxyl group at the 2-position. Naturally, it is necessary to separate these diastereomers after the lactone formation, with the result that the yield of the desired product in which an S-arrangement is formed with respect to the carbon atom at the 2-position is as low as about 30%.

In addition, as many as six process steps are required for preparing the direct starting material of hydroxy aldehyde itself having an optical activity from L-malic acid, and the yield thereof is only 25%. It follows that as many as 11 process steps are required for manufacturing 3-DPA-lactone from L-malic acid. Further, if the removal of one diastereomer is taken into account, the total yield is as low as only about 4%.

In the known method using γ-ribonolactone as the starting material, the hydroxyl group of γ-ribonolactone is protected by an acetyl group, followed by applying a catalytic hydrogenation under a high pressure in the presence of palladium-carbon as a catalyst so as to achieve deacylation and, thus, to refine 3-DPA-lactone. In this method, however, it is necessary to carry out the catalytic hydrogenation under such a high pressure as 100 atms., making it necessary to use a complex apparatus. In addition, a problem remains unsolved in terms of safety.

DISCLOSURE OF THE INVENTION

An object of the present invention is to provide a method of manufacturing 3-DPA-lactone, which permits easily and selectively synthesizing 3-DPA-lactone in a high yield from readily available raw materials.

As a result of an extensive research made in an attempt to achieve the object noted above, the present inventors have found it possible to manufacture 3-DPA-lactone more easily and in a higher yield than in the prior art by regioselectively or stereoselectively carrying out the protection of a hydroxyl group, elimination reaction, catalytic hydrogenation reaction, etc. using γ-ribonolactone as a starting material.

According to the present invention, there is provided a method of manufacturing 3-DPA-lactone, comprising the steps of:

(a) protecting the roxyethym group at 4-position of γ-ribonolactone represented by formula (I) given below so as to obtain a compound represented by general formula (II) given below:

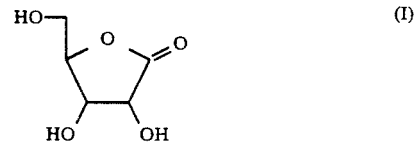
(I)

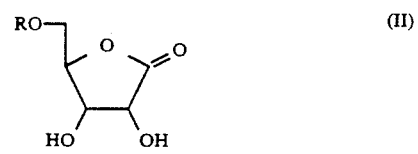
(II)

where R is a protective group of the hydroxyl group; 1 (b) eliminating the hydroxyl group the 3-position of the compound represented by general, formula (II) so as to form a double bond between the 2- and 3-positions and, thus, to form a compound having the hydroxyl group at the 2-position protected, which is represented by general formula (III) given below:

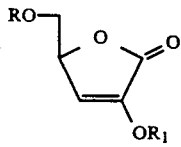

where each of R and $R_1$ represents the protective group of the hydroxyl group;

(c) reducing the double bond formed between the 2- and 3-positions of the compound represented by general formula (III) so as to obtain a compound represented by general formula (IV) given below:

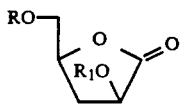

where R and $R_1$ are as defined in conjunction with general formula (III); and (d) eliminating the protective groups of the compound represented by general formula (IV) so as to obtain a compound represented by formula (V) given below:

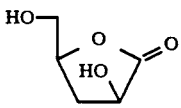

BEST MODE FOR CARRYING OUT THE INVENTION

Each step of the method of the present invention for manufacturing 3-DPA-lactone is carried out as follows.

In step (a), a protective group R is introduced into 4-position of γ-ribonolactone represented by formula (I). Any atomic group generally used for protecting a hydroxyl group can be used as protective group R. For example, acetyl, benzoyl, 3,5-dinitrobenzoyl and tert-butyl-diphenyl silyl groups can be effectively used as protective group R. Also, an organic solvent used in general can be used in step (a) for introducing protective group R, though the solvent is not particularly restricted in the present invention.

In step (b), the hydroxyl group at the 3-position of the compound represented by general formula (II), which is obtained in step (a), is eliminated (β-elimination) so as to form a double bond between the 2- and 3-positions of the compound. The β-elimination can be easily performed by adding an acylating agent to the compound represented by general formula (II) and stirring the mixture in the presence of a suitable basic compound at room temperature or under heating.

The acylating agent used in step (b) includes, for example, an acid anhydride such as acetic anhydride and an acid chloride such as acetylchloride. On the other hand, the basic compound used in step (b) includes tertiary amine compounds such as triethylamine and dimethylaminopyridine.

As pointed out above, the β-elimination is carried out in the compound represented by general formula (II) by using an acylating agent and a basic compound together. At the same time, the hydroxyl group at the 2-position of the compound is protected by protective group $R_1$ so as to obtain a compound of general formula (III).

In step (c), the double bond between the 2- and 3-positions of the compound represented by general formula (III) is reduced so as to obtain a compound represented by general formula (IV). A catalytic hydrogenation can be employed for the reduction. For example, the double bond can be easily reduced by stirring at room temperature the compound of general formula (III) dissolved in a suitable organic solvent under a hydrogen gas atmosphere and in the presence of a suitable metal catalyst such as platinum, palladium, rhodium, or ruthenium. A general organic solvent such as ethyl acetate, ethanol or methanol can be used in step (c), through the solvent is not particularly restricted in the present invention.

Finally, the protective groups at the 2- and 4-positions of the compound represented by general formula (IV) are eliminated in step (d) so as to obtain 3-DPA-lactone represented by formula (V).

The reaction for eliminating the protective group can be carried out under any condition under which an acyl group or silyl ether group is generally eliminated and, thus, is not particularly restricted in the present invention. For example, the acyl group can be eliminated under basic conditions using a metal hydroxide such as sodium hydroxide or potassium hydroxide, a metal carbonate such as sodium carbonate or potassium carbonate, a metal alkoxide such as sodium methoxide or potassium butoxide, or ammonia water, within an aqueous solution in the presence of an acid such as hydrochloric acid or paratoluene sulfonic acid, or under acidic conditions using an organic solvent such as an alcohol.

The formed product is subjected to measurement with $^1$H-NMR spectrum and $^{13}$C-NMR spectrum, and the measured values are compared with values shown in literature "O. Uchikawa, N. Okukado, T. Sakata, K. Arase, K. Terada, Bull, Chem, Soc. Jpn., 61,2025 (1988)" so as to confirm that the formed product is 3-DPA-lactone.

The present invention will be described in detail by way of the following Example.

EXAMPLE 1

In the Example, the hydroxy-methyl group at 4-position is protected in step 1 as a silyl ether, and an elimination reaction is carried out in step 2 such that the hydroxyl group in the 2-position is protected as an acetyl group.

(Step 1) ... Synthesis of 5-O-(tert-butyl-diphenylsilyl)-ribonolactone 10.0 g (67.5 mmol) of ribonolactone and 5.04 g (74.0 mmol) of imidazol were dissolved in 50 ml of dimethyl formamide, followed by dripping 20.3 g (74.0 mmol) of tert-butyl-diphenylsilyl chloride into the resultant solution. The resultant mixture was kept stirred at room temperature for 1 hour. The reaction solution thus obtained was poured into a suitable amount of water and, then, extracted with diethyl ether, followed by drying with magnesium sulfate. Further, the solvent was removed by distillation under a reduced pressure.

(Step 2)

The residue obtained in step 1 was dissolved in 300 ml of methylene chloride, followed by adding 15.1 g (149 mmol) of triethyl amine, 1 g (8.2 mmol) of dimethylaminoptridine and 15.2 g (149 mmol) of acetic anhydride in this order to the resultant solution. The resultant mixture was kept stirred at room temperature for 2.5 days. Then, the reaction solution was poured into a suitable amount of an aqueous solution of sodium hydrogencarbonate and, then, extracted with ethyl acetate, followed by drying with magnesium sulfate. Further, the solvent was removed by distillation under a reduced pressure. The residue thus obtained was refined with a silica gel column chromatograph (hexane:ethyl acetate=5:1) so as to obtain 21.5 g of the formed product (yield of 77.5% based on the starting material).

$^1$H-NMR (CDCl$_3$, ppm from TMS): (CH$_3$)$_3$CSi:1.07 (9H, s), CH$_3$CO:2.31 (3H, S), C$_6$H$_5$Si:7.37–7.48 (6H, m), 7.62–7.65 (4H, m), 3-position:7.20 (1H, d, J=1.9 Hz), 4-position:5.06 (1H, ddd, J=1.9, 4.5 4.6 Hz), 5-position:3.86 (1H, dd, J=4.5, 11.0 Hz), 3.92 (1H, dd, J=4.6, 11.0 Hz)

(Step 3)

9.41 g (22.9 mmol) of the compound obtained in step 2 was dissolved in 100 ml of ethyl acetate, followed by adding 1 g of 10% palladium-carbon to the resultant solution. The mixture thus prepared was kept stirred at room temperature for 18 hours under a hydrogen gas atmosphere. Then, the palladium-carbon was removed by filtration from the reaction solution, followed by removing the solvent from the filtrate by means of distillation so as to obtain 9.6 g of residue.

$^1$H-NMR (CDCl$_3$, ppm from TMS): (CH$_3$)$_3$CSi:1.06 (9H, s), CH$_3$CO:2.17 (3H, s), C$_6$H$_5$Si:7.38–7.48 (6H, m), 7.64–7.68 (7.64–7.68 (4H, m), (Step 4)

(a) 9.60 g of the residue obtained in step 3 was dissolved in 3980 ml of methanol, followed by adding 15.9 g of potassium carbonate to the resultant solution. The resultant mixture was kept stirred for 2 hours at room temperature. Then, 1 N hydrochloric acid was slowly dripped into the reaction mixture under cooling with ice-water so as to neutralize the reaction mixture, followed by removing methanol by distillation under a reduced pressure. Further, the reaction mixture was extracted with diethyl ether and, then, dried with magnesium sulfate, followed by removing the solvent by distillation under a reduced pressure.

The residue thus obtained was refined with a silica gel column chromatograph (hexane:diethyl ether=3:1 to 2:1; hexane:ethyl acetate=2:1) so as to obtain 4.96 g of the formed product (yield of 58.4% based on the reaction product obtained in step 2). The formed product thus obtained was further recrystallized from a hexane/diethyl ether mixed solvent (mixing ratio of 1:2) so as to obtain 2.69 g of a compound represented by formula (VI) given below (yield of 31.7% based on the product obtained in step 2):

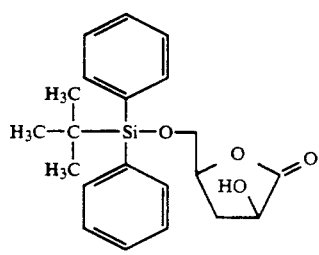
(VI)

melting point:107.4–109.1° C. [α $D^{27}$ −0/81° (C=2.09, CH$_3$OH)

IR $\nu_{max}$ 3396 (m), 2960 (m), 2930 (m), 2862 (m), 1760 (s), 1470 (w), 1429 (w), 1354 (w), 1197 (m), 1172 (m), 1135 (s), 1114 (s), 1017 (m), 978 (m), 930 (w), 888 (w), 824 (m), 799 (m), 750 (m), 710 (s), 623 (m), 598 (m), 505 (s), $^1$H-NMR (CDCl$_3$, ppm from TMS):
(CH$_3$)$_3$CSi:1.06 (9H, s), C$_6$H$_5$Si:7.37–7.48 (6H, m), 7.65–7.68 (4H, m), OH:2.96 (1H, d, J=3.9 Hz), 2-and 4-positions:4.48–4.56 (2H, m), 3-position:2.23 (1H, ddd, J=9.4, 9.5, 12.8 Hz), 2.60 (1H, ddd, J=6.0, 8.6, 12.8 Hz), 5-position:3.73 (1H, dd, J=4.1, 11.6 Hz). 3.91 (1H, dd, J=3.3, 11.6 Hz)

(b) 0.42 g (1.12 mmol) of the compound represented by formula (VI) given above was dissolved in 10 ml of tetrahydrofuran, followed by adding 1.2 ml of a tetrahydrofuran solution of 1 M tetra(n-butyl) ammonium fluoride to the resultant solution. The resultant mixture was kept stirred at room temperature for 1 hour. Then, the solvent of the mixture was removed by distillation under a reduced pressure. Further, the residue was refined with a silica gel column chromatograph (ethyl acetate) so as to obtain 0.10 g of an oily product of (2S, 4S)-2-hydroxy-4-hydroxymethyl-4-butanolide (3-DPA-lactone) (yield of 68.3%).

$^1$H-NMR (CD$_3$OD, ppm from TMS): 2-position:4.59 (1H, dd, J=8.5, 10.8 Hz), 3-position:1.98 (1H, ddd, J=10.6, 10.8 12.3 Hz), 2.56 (1H, ddd, J=5.6, 8.5, 12.3 Hz), 4-position:4.45–4.53 (1H, m), 5-position:3.60 (1H, dd, J=5.0, 12.7 Hz), 3.82 (1H, dd, J=2.9, 12.7 Hz)
$^{13}$C-NMR (CD$_3$OD, ppm from CD3OD (CD3:49.8 ppm)): 179.1, 78.5, 69.2, 63.7, 33.4.

As described previously, the present invention makes it possible to easily and selectively synthesize 3-DPA-lactone, which is hardly obtained from natural materials in a large amount, in high yield from readily available raw materials in a small number of steps compared with the conventional method. In recent years, saccharide-containing compounds and saccharide-like compounds have attracted attention as useful physiologically active substances in the field of fine chemicals such as medicines and agricultural chemicals. Under the circumstance, the present invention makes it possible to readily supply 3-DPA-lactone which is one of the useful physiologically active substances and is known as an appetite-promoting substance.

We claim:

1. A method of manufacturing 3-DPA-lactone, comprising the steps of:
(a) protecting the hydroxymethyl group at the 4-position of γ-ribonolactone represented by formula (I) given below so as to obtain a compound represented by formula (II) given below:

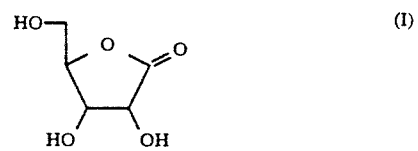
(I)

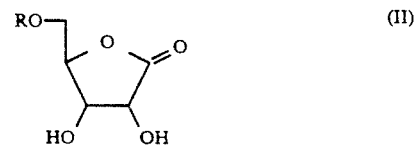
(II)

where R is a protective group of said hydroxyl group;

(b) eliminating the hydroxyl group at the 3-position of the compound represented by formula (II) so as to form a double bond between the 2- and 3-positions and, thus, to form a compound having the hydroxyl group at the 2-position protected, which is represented by formula (III) given below:

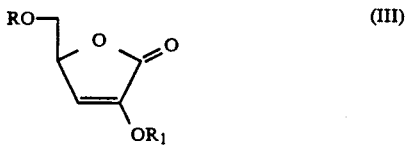

where each of R and $R_1$ represents a protective group;

(c) reducing said double bond formed between said 2- and 3-positions of said compound represented by formula (III) so as to obtain a compound represented by formula (IV) given below:

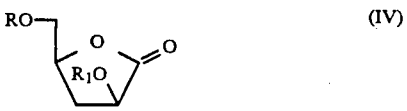

where R and $R_1$ are as defined as in conjunction with formula (III); and (d) eliminating the protective groups of said compound represented by formula (IV) so as to obtain a compound represented by formula (V) given below:

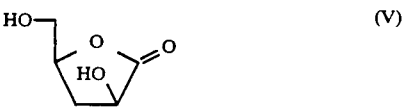

2. The method of claim 1, wherein said protective group of step (a) is a member selected from the group consisting of an acetyl group, a benzoyl group, a 3,5-dinitrobenzoyl group, and a tert-butyl-diphenyl silyl group.

3. The method of claim 1, wherein said eliminating of step (b) is performed by adding an acylating agent to said compound (II) and stirring the resulting mixture in the presence of a basic compound at room temperature or under heating.

4. The method of claim 3, wherein said acylating agent is an acid anhydride or an acid chloride.

5. The method of claim 4, wherein said acid anhydride is acetic anhydride and said acid chloride is acetylchloride.

6. The method of claim 3, wherein said basic compound is a tertiary amine.

7. The method of claim 6, wherein said tertiary amine is a member selected from the group consisting of triethylamine and dimethylaminopyridine.

8. The method of claim 1, wherein said reducing of step (c) is performed by catalytic hydrogenation.

9. The method of claim 8, wherein said catalytic hydrogenation is performed by stirring said compound (III) at room temperature in an organic solvent under a hydrogen gas atmosphere in the presence of a metal catalyst selected from the group consisting of platinum, palladium, rhodium, and ruthenium.

10. The method of claim 9, wherein said organic solvent is a member selected from the group consisting of ethyl acetate, ethanol, and methanol.

11. The method of claim 1, wherein said eliminating of step (d) is carried out under basic conditions using a metal hydroxide selected from the group consisting of sodium hydroxide and potassium hydroxide, a metal carbonate selected from the group consisting of sodium carbonate and potassium carbonate, a metal alkoxide selected from the group consisting of sodium methoxide and potassium butoxide, or ammonia water.

12. The method of claim 1, wherein said eliminating of step (d) is carried out under acidic conditions in an aqueous solution of an acid selected from the group consisting of hydrochloric acid and paratoluenesulfonic acid.

13. The method of claim 1, wherein said eliminating of step (d) is carried out under acidic conditions using an organic solvent.

14. The method of claim 13, wherein said organic solvent is an alcohol.

* * * * *